United States Patent [19]

Kienle

[11] Patent Number: 5,112,610

[45] Date of Patent: May 12, 1992

[54] **METHOD OF MAKING A NATURAL SWEETENER BASED ON *STEVIA REBAUDIANA*, AND USE THEREOF**

[76] Inventor: Udo Kienle, Weidachstrasse 12, 7000 Stuttgart 70, Fed. Rep. of Germany

[21] Appl. No.: 586,690

[22] Filed: Sep. 24, 1990

[51] Int. Cl.$^5$ .................. A61K 35/78; C07H 15/24
[52] U.S. Cl. .................. 424/195.1; 536/18.1; 426/548
[58] Field of Search .............. 424/195.1; 536/18.1; 426/48, 548

[56] References Cited

U.S. PATENT DOCUMENTS

| | | | |
|---|---|---|---|
| 4,024,334 | 5/1977 | Chandler | 536/65 |
| 4,082,858 | 4/1978 | Morita | 426/597 |
| 4,219,571 | 8/1980 | Miyake | 426/48 |
| 4,554,170 | 11/1985 | Panzner | 426/651 |
| 4,592,911 | 6/1986 | Behr | 424/195.1 |
| 4,599,403 | 7/1986 | Kumar | 536/18.1 |
| 4,601,906 | 7/1986 | Shindler | 424/195.1 |
| 4,612,942 | 9/1986 | Dobblerstein | 131/276 |

FOREIGN PATENT DOCUMENTS 0335265 3/1989 European Pat. Off. .
62-00496 1/1987 Japan .

OTHER PUBLICATIONS

A. I. Bakal & L. O'Brien Nabors, "Stevioside" in Alternative Sweeteners, Marcel Dekker Inc., N.Y. 1986, pp. 295–307.

*Primary Examiner*—Ronald W. Griffin
*Assistant Examiner*—Ralph Gitomer
*Attorney, Agent, or Firm*—Henry M. Feiereisen

[57] ABSTRACT

A method of making a natural sweetener based on *Stevia rebaudiana* includes extraction of plant parts of *Stevia rebaudiana* with a solvent to provide an extract, and subjecting the extract to an extraction with a supercritical gas to obtain an extraction residue which is freed from undesired and taste-impairing constituents.

18 Claims, No Drawings

METHOD OF MAKING A NATURAL SWEETENER BASED ON *STEVIA REBAUDIANA*, AND USE THEREOF

BACKGROUND OF THE INVENTION

The invention refers to a method of making a natural sweetener based on Stevia rebaudiana, and use thereof.

As set forth in the article entitled "Stevioside", page 295 to 307 by Abraham I. Bakal and Lyn O'Brien Nabors in the publication "Alternative Sweeteners", Marcel Dekker Inc., New York 1986 as well as in the various citations referred to in that article, the plant Stevia rebaudiana is native in South America and is used as traditional sweetener for mate tea. The components of this plant are characterized by a high sweetness intensity so that tests were undertaken to cultivate this plant not only in its native countries but also in East Asia and to commercially exploit extracts obtained therefrom. The sweetness of the plant parts and of the extracts obtained therefrom can be attributed to a number of chemical substances which all belong to the class of diterpene glycosides. The most important singular compounds are the stevioside and rebaudiside A which have the following chemical structure:

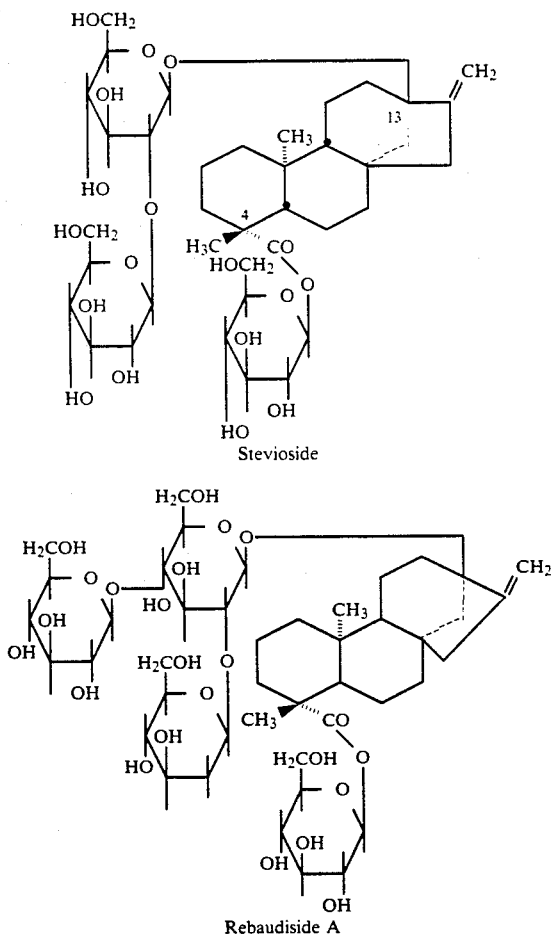

Stevioside

Rebaudiside A

Aside from these two compounds, further compounds could be identified which contribute to the sweetness intensity.

In order to make sweeteners from Stevia rebaudiana, the plant parts, usually the dried leaves, are extracted with water or with an organic solvent such as alcohol. The extracts are then subjected to various refining steps for purifying and enrichment of the components effecting the sweetness intensity. These refining steps may encompass the following process types: precipitation of contaminants by means of inorganic salts and subsequent treatment of the extract with ion-exchangers, precipitation of the contaminations through controlled variation of the pH value, precipitation of undesired accompanying substances through aggregation on polymers or fixed adsorbents, purification through chromatographic steps, purification through adsorption on pigments; liquid extraction; electrophoresis, membrane filtration.

The number of publications cited in Chemical Abstracts volumes 85–105, which primarily are published Japanese patent applications, is above 70. Products which are obtained from raw extracts and have improved sweetness intensity are also disclosed for example in the U.S. Pat. Nos. 4,082,858 and 4,219,571, with the latter patent specification referring to an enzymatic production method.

The sweetness intensity of the extract, which sometimes is simply called "stevioside", is usually about 150 to 300 times the sweetness intensity of sucrose depending on the used concentration.

The reason that kept sweeteners derived from Stevia rebaudiana from being introduced in Europe and North America is a bitter and astringent aftertaste which frequently is also described as menthol-like. In all known, commercially applicable methods, this aftertaste remains in the extract and leaves a greatly impaired taste, especially at high purity of the extract or at high concentration. Although such taste or aftertaste has been tolerated in countries in which sweeteners based on Stevia rebaudiana are used in foodstuffs and beverages, a product of such quality would not be accepted by consumers in Europe or North America. Further, the bitter aftertaste also limits the application of sweeteners of Stevia rebaudiana for use in alcohol-free beverages such as soft drinks.

SUMMARY OF THE INVENTION

It is an object of the present invention to provide a natural sweetener based on Stevia rebaudiana obviating the afore-stated drawbacks.

In particular, it is an object of the present invention to provide a natural sweetener on the basis of an extract obtained from plant parts of Stevia rebaudiana without encountering an undesired aftertaste, and yet retaining its full sweetness intensity.

These objects and others which will become apparent hereinafter are attained in accordance with the present invention by separating from the plant parts an extract through extraction with a solvent, and extracting the extract with a supercritical gas for obtaining an extraction residue which is freed from undesired and taste-impairing constituents.

Through the provision of the method according to the present invention, the undesired aftertaste is removed thus rendering the obtained sweeteners applicable for a wide range of foodstuffs and beverages, especially for soft drinks, and thence for products for which extracts from Stevia rebaudiana were unsuitable to date. It has been surprisingly found that the extraction with supercritical gases attains a complete or nearly complete removal of those components of Stevia rebaudiana which cause the bitter or astringent aftertaste. This is also true for all commercially available extracts or enzymatic transformation products.

None of the numerous citations discloses an extraction method with supercritical gases, in particular with supercritical carbon dioxide in order to remove the distasteful components of the Stevia rebaudiana plant which not only are found in the leaves of Stevia rebaudiana but also in all extracts and in the enzymatic transformation products of stevioside.

It has further been found that the use of liquid carbon dioxide as extractant can also provide an effective removal of the bitter and astringent components of Stevia rebaudiana although the degree of effectiveness of supercritical carbon dioxide is not attained.

The product obtained after extraction with supercritical gas i.e. the extraction residue has a considerable improved taste. The field of application is increased to such extent that higher sweetness concentrations are attained, e.g. for soft drinks, without diminishing the acceptance by the consumer.

A method of extraction with supercritical gases is known per se as summarized in the publication by E. Stahl, K. W. Quirin, D. Gerard, entitled "Verdichtete Gase zur Extraktion und Raffination", Springer-Verlag, Berlin, Heidelberg, New York, London, Paris, Tokyo, 1987 to which reference is made herewith.

The Japanese patent JP-A- 62-000496 discloses the attempt to extract the sweetener stevioside from leaves of Stevia rebaudiana with supercritical carbon dioxide. As set forth therein, the use of supercritical carbon dioxide does not enable extraction of stevioside unless 0.5 to 50 mol-% methanol, ethanol or acetone or a tertiary mixture of supercritical carbon dioxide, water and methanol is added. Stevioside obtained by such extraction is contaminated by numerous undesirable constituents and especially contaminated with taste-impairing components. For purposes of purification, in particular purification of a conventionally obtained stevioside extract, the extraction method with supercritical carbon dioxide is not considered.

DETAILED DESCRIPTION

The method according to the present invention uses as extraction a supercritical gas for refining stevia-extracts of all types. It has been found that the desired results are attained when using a number of gases although the individual gases differ in their effectiveness to a certain degree. The removal of bitter and astringent constituents of Stevia rebaudiana are better attained by ethane, ethene, nitrous oxide, propane and propene than by carbon dioxide or various hydrogen fluorides.

However, since organic extractants has commonly known drawbacks and nitrous oxide supports the burning and thus must be handled with great care, carbon dioxide has proven to be the preferred gas for carrying out the method according to the present invention.

Modifications of the method according to the present invention, especially the critical temperatures and pressures as well as densities for the above-mentioned other extractants, are discussed in the prior art publication (see e.g. the publication by E. Stahl et al, as referred above, page 15). In contrast to the other above-stated gases, carbon dioxide is physiologically safe, non-combustible or explosive, not harmful to the environment and is available in great amounts. Moreover, extraction methods using supercritical carbon monoxide are well documented.

Carbon dioxide is raised to supercritical conditions (pressure above 72.9 bar, temperature above 31° C.) by a pressure generator and raised to the extraction temperature isobarically by means of a heat exchanger. Subsequently, the supercritical carbon dioxide of desired temperature is fed in an extraction vessel containing the raw material to be treated. At continuous process, the supercritical carbon dioxide is led through the material being extracted.

After extraction, the extract-laden gas is relaxed to a pressure below 72.9 bar. The gas cools down and is present as wet steam, with formation of a liquid extract-enriched phase and a gas extract-enriched phase. For separation, the gas is vaporized and isobarically brought to the temperature of separation, suitably between 25° and 50° C. After separation, the regenerated gas is cooled down to liquefaction temperature and returned to the process.

Basically, the method according to the invention follows these method steps. The temperature of extraction should be in the range between 31° C. and 100° depending on the used starting material. In order to attain an effective extraction of the taste-impairing constituents, a sufficient mass rate of the starting material being treated and the quantity of carbon dioxide should be provided for.

It should be noted, however, that the temperature of extraction may exceed 100° C., provided an extract of Stevia rebauidiana is used which is obtained with organic solvent boiling above 100° C.

According to a further feature of the present invention, the relative mass rate can be varied between 5 kg $CO_2$/kg starting material and up to 310 kg $CO_2$/kg starting material. Generally, the mass ratio lies between 8 kg $CO_2$/kg starting material and 100 kg $CO_2$/kg starting material. A mass ratio below 5 kg $CO_2$/kg starting material will not result in a marked removal of undesired flavorings.

An optimal ratio of the relative mass rates at preferred conditions of 60° C. and 300 bar ranges between 8 and 100 kg $CO_2$/kg starting material.

When using liquid carbon dioxide, the temperatures may range from 0° to 31° C., preferably from 5° to 31° C. and the pressures may range from 40 to 72.9 bar. The process steps in case liquid carbon dioxide is employed as extractant are similar to the process steps with supercritical carbon dioxide, except there is no necessity of expanding the extract-laden extraction to subcritical pressure.

The treatment of the starting material with carbon dioxide in a manner as described herein results in a raffinate which can be utilized as sweetener in soft drinks in suitable concentration without impairment in taste. The sweetener has superior sweetness properties in comparison to known synthetic sweeteners and is characterized by a flavor profile which is similar to sugar taste.

In the following, the method according to the invention will be described in more detail by way of examples.

EXAMPLE 1

Treatment of Leaves of Stevia rebaudiana Bertoni

Whole or comminuted, fresh or dried leaves of Stevia rebaudiana Bertoni are introduced in an extraction vessel. After sealing the extraction vessel, supercritical carbon dioxide is fed through the vessel for removing cuticle waxes, chlorophyll, other pigments and especially taste-impairing components. The substances removed from the leaves and solved in the supercritical carbon dioxide are separated in the vessel to thereby regenerate the carbon dioxide which can then be returned to the process after suitable compression.

After ending the extraction process which takes about 8 hours, the vessel is opened and the plant parts are withdrawn for direct use or for subsequent aftertreatment in known manner like fresh or dried leaves to thereby isolating the sweet diterpene glycosides without impairment to the flavor.

This process, however, requires a great quantity of starting material so that the use of leaves has shown to be less economical even when increasing the bulk density of the dried or comminuted leaves by pressing into pellets prior to the extraction.

Example 2

Treatment of Powder Extracts from Leaves of Stevia rebaudiana Bertoni

A powdered extract, which is obtained from leaves of Stevia rebaudiana Bertoni by conventional methods, is introduced in an extraction vessel and treated with supercritical carbon dioxide. If suitable, water, a $C_1$-$C_4$-alcohol or a suitable hydrocarbon or a mixture of the above-mentioned solvents may be added to the gas as entrainer.

Also in this case, the taste-impairing flavors are substantially removed from the extraction residue which constitutes the sweetener product. This type of treatment allows a removal of taste-impairing components only to a lesser degree, and without employing entrainers achieves not entirely satisfactory results. Moreover, the thermal strain may also prove disadvantageous. In order to avoid quality impairment, an extraction temperature of 50° C. should not be exceeded.

EXAMPLE 3

Treatment of Extract Solutions from Leaves of Stevia rebaudiana Bertoni

Extract solutions containing an extract of leaves of Stevia rebaudiana Bertoni in water or suitable alcohol or any other suitable organic solvent or mixture of solvents are continuously pumped in an extraction vessel which is filled with packings for increasing the contact area between liquid and gas. The gas flow and the addition of liquid extract are adjusted to each other in such a manner that the relative mass flow in the extract solution ranges between 8 and 50 kg $CO_2$/kg solids. Extraction pressure and extraction temperature lie in the supercritical range, with preferred condition being 300 bar and 60° C.

An extraction method of this type is preferred and allows substantial removal of taste-impairing components and other contaminants. The purity of the liquid extract is not crucial, and thus may be a crude extract, or may partly or completely be purified by conventional methods, or an additional purification may be provided after treatment in accordance with the present invention.

When using as solvent an alcohol or an organic solvent, the extract solutions should be aqueous and at least have a minimum water content in order to allow the purified sweetener solved in an own aqueous phase to be continuously withdrawn.

In case, extract solutions in alcoholic solvents or other organic solvents are used, it is suitable to recover the solvent by known methods for keeping the amount of solvent to be used to a minimum.

In the event, the extract employed in the method according to the present invention has a sufficiently high degree of purity (sweetener content of more than 40%), the treated extract, i.e. the extraction residue can be directly added in liquid form to foodstuffs or beverages provided the solvent permits such proceeding.

EXAMPLE 4

Purification of Raw Stevioside and Other Sweet Substances Isolated from Stevia rebaudiana Bertoni as well as of Enzymatic Transformation Products of Raw Stevioside In a manner known per se, stevioside and rebaudiside A are separated as pure substance from extracts of Stevia rebaudiana. The substances are initially obtained in crystalline form as raw stevioside and raw rebaudiside A which contain a number of contaminants deposited upon the crystal surface and causing even in this isolated form the taste-impairing characteristics as set forth above.

In accordance with the present invention, for refining purposes, the raw stevioside and the raw rebaudiside A is solved in a known manner. The obtained solution is fed continuously in an extraction vessel in a manner set forth in Example 3, with the taste-impairing substances being removed as described in the previous examples. The purified and taste-improved stevioside and rebaudiside A may be added to the foodstuffs and beverages.

Likewise, solutions of raw stevioside which are enzymatically transformed into rebaudiside A may be treated in accordance with the method of the present invention for obtaining a taste-enhanced natural sweetener. Raw stevioside may be enzymatically transformed through various methods either into $\alpha$-glycosylated Stevia sweetener or into rebaudisine A. This is also true for enzymatically transformed solutions of raw stevioside $\alpha$.

In order to be used in the field of food technology or by the end consumer, the refined sweetener according to the present invention may be prepared in various conventional manner. As previously set forth, purified extract solutions may be directly added in liquid form. It is, however, also feasible, to convert the purified extracts or the purified stevioside or rebaudiside A into a solid crystalline form and to make it commercially available in this form. In view of its high sweetness intensity, stevia-extracts may be suitably diluted with a tasteless diluent when being used by the end consumer as sweetener for beverages such as tea or coffee. The sweetener i.e. the Stevia-extract is suitably diluted with soluble starch and commercially packed for distribution in small paper bags, with a sweetness intensity comparable to one piece of lump sugar.

While the invention has been illustrated and described as embodied in a method of making a natural sweetener based on Stevia rebaudiana, and use thereof, it is not intended to be limited to the details shown since various modifications and structural changes may be made without departing in any way from the spirit of the present invention.

What is claimed as new and desired to be protected by Letters Patent is set forth in the appended claims:

1. A method of making a natural sweetener substantially free of bitter aftertaste from an extract obtained from plant parts of Stevia rebaudiana; comprising the step of extracting said extract with a supercritical gas to obtain an extraction residue.

2. A method as defined in claim 1 wherein the supercritical gas is selected from the group consisting of carbon dioxide, ethane, ethene, nitrous oxide, propane and propene.

3. A method as defined in claim 1 with the supercritical gas being carbon dioxide and being at a temperature in the range of 31° to 100°, at a pressure above 72.9 bar and at a quantity, relative to the dry substance of the starting material subjected to extraction, of 5 to 310 kg $CO_2$/kg dry substance.

4. A method as defined in claim 3 wherein the temperature of the supercritical carbon dioxide ranges between 50° and 70° and the pressure ranges between 100 and 400 bar, with the quantity of supercritical carbon dioxide being in the range of 8 to 310 kg $CO_2$/kg dry substance.

5. A method as defined in claim 4 wherein the pressure of the supercritical carbon dioxide ranges between 250 and 350 bar.

6. A method as defined in claim 1 wherein the extract is present in form of a solution in an aqueous solvent.

7. A method as defined in claim 1 wherein the extract is present in form of a solution in an organic solvent.

8. A method as defined in claim 1 wherein said step of extracting the extract is performed in an extraction vessel filled with packings, with the flow of supercritical gas being adjusted to the supplied amount of extract in such a manner that the relative mass ratio ranges between 5 to 50 kg $CO_2$/kg dry substance.

9. A method as defined in claim 8 wherein the mass ratio ranges between between 8 to 50 kg $CO_2$/kg dry substance.

10. A method as defined in claim 1 wherein the extract subjected to extraction with supercritical gas is aqueous.

11. A method as defined in claim 1 wherein the extract is solid and in powder form, said extracting step being carried out at an extraction temperature below 50° C.

12. A method as defined in claim 1 wherein said extracting step is carried out in the presence of an entrainer.

13. A method of making a natural sweetener from Stevia rebaudiana; comprising the steps of:
providing as starting material plant parts of Stevia rebaudiana;
extracting the plant parts with a solvent to provide an extract; and
subjecting the extract to an extraction with a supercritical gas to obtain an extraction residue.

14. A method of making a natural sweetener from Stevia rebaudiana; comprising the steps of:
introducing as starting material plant parts of Stevia rebaudiana in an extraction vessel; and
separating from the plant parts an extract by feeding a supercritical gas into the extraction vessel so as to obtain an extraction residue.

15. A method of making a natural sweetener from an extract obtained form plant parts of Stevia rebaudiana; comprising the step of extracting the extract with liquid carbon dioxide to obtain an extraction residue.

16. A method as defined in claim 15 comprising extracting with liquid carbon dioxide at a temperature ranging from 0° to 31° and at a pressure ranging from 40 to 72.9 bar.

17. A method as defined in claim 15 comprising extracting with liquid carbon dioxide at a temperature ranging from 5° to 31°.

18. A method of making a natural sweetener substantially free of bitter aftertaste, from α-glycosylated stevioside or rebaudiside A, comprising the step of extracting said α-glycosylated stevioside or rebaudiside A with a super-critical gas to obtain an extraction residue.

* * * * *